(12) United States Patent
Yoon et al.

(10) Patent No.: US 7,935,733 B2
(45) Date of Patent: May 3, 2011

(54) CARBON NANOTUBE SOLUTION DISPERSANT AND COMPOSITION INCLUDING THE SAME

(75) Inventors: Seon Mi Yoon, Yongin-si (KR); Jeong Hee Lee, Seongnam-si (KR); Eun Sung Lee, Seoul (KR); Jae Young Choi, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 342 days.

(21) Appl. No.: 11/446,972

(22) Filed: Jun. 6, 2006

(65) Prior Publication Data

US 2007/0057233 A1 Mar. 15, 2007

(30) Foreign Application Priority Data

Jul. 27, 2005 (KR) ........................ 10-2005-0068346

(51) Int. Cl.
*B01F 3/12* (2006.01)
(52) U.S. Cl. ............... 516/32; 516/56; 516/77; 502/101
(58) Field of Classification Search .................... 516/32, 516/56, 77; 977/742
See application file for complete search history.

(56) References Cited

U.S. PATENT DOCUMENTS

| | | | | |
|---|---|---|---|---|
| 4,097,297 | A * | 6/1978 | Keene ................... | 106/169.14 |
| 4,145,382 | A * | 3/1979 | Hayashi et al. ................. | 558/92 |
| 4,627,999 | A * | 12/1986 | Hsu ................................. | 428/326 |
| 5,688,884 | A * | 11/1997 | Baker et al. ................... | 526/225 |
| 6,028,066 | A * | 2/2000 | Unger ............................ | 514/180 |
| 6,258,772 | B1 * | 7/2001 | Yeggy et al. ................... | 510/422 |
| 6,783,746 | B1 * | 8/2004 | Zhang et al. ................. | 423/447.1 |
| 7,160,374 | B2 * | 1/2007 | Umehara et al. .............. | 106/31.6 |
| 2003/0176572 | A1 * | 9/2003 | Maekawa et al. ............. | 524/805 |
| 2004/0021131 | A1 * | 2/2004 | Blanchet-Fincher et al. | 252/500 |
| 2004/0038251 | A1 * | 2/2004 | Smalley et al. .................... | 435/6 |
| 2004/0102577 | A1 * | 5/2004 | Hsu et al. ....................... | 525/182 |
| 2004/0197638 | A1 * | 10/2004 | McElrath et al. ............... | 429/44 |
| 2005/0261141 | A1 * | 11/2005 | Iso et al. ........................ | 508/154 |

FOREIGN PATENT DOCUMENTS

JP 2004-130306 * 4/2004

OTHER PUBLICATIONS

"Aldrich Zonyl FSA fluorosurfactant" for product specification, Feb. 2004.*
Zonyl FSE phosphate fluorosurfactant for product specification, 1986.*

* cited by examiner

*Primary Examiner* — Ling-Siu Choi
*Assistant Examiner* — Chun-Cheng Wang
(74) *Attorney, Agent, or Firm* — Harness, Dickey & Pierce, P.L.C.

(57) ABSTRACT

A dispersant for a more concentrated carbon nanotube solution, and a composition including the same are provided. The dispersant may have a hydrophobic chain structure with head groups capable of surrounding carbon nanotube particles. The dispersant may adsorbed onto the carbon nanotube particles. The composition may include the dispersant, an aqueous liquid medium and a carbon nanotube. The composition may further include an additive. It may be possible to produce a more concentrated carbon nanotube solution exhibiting an increase in dispersion of the carbon nanotube particles and/or more stability.

13 Claims, 3 Drawing Sheets

CARBON NANOTUBE SOLUTION DISPERSANT AND COMPOSITION INCLUDING THE SAME

PRIORITY STATEMENT

This application claims priority under 35 USC §119 to Korean Patent Application No. 10-2005-68346 filed on Jul. 27, 2005, in the Korean Intellectual Property Office, the contents of which is herein incorporated by reference in its entirety.

BACKGROUND OF THE INVENTION

1. Field of the Invention

Example embodiments of the present invention provide a dispersant for a carbon nanotube solution and a composition including the same. Other example embodiments of the present invention provide a dispersant having a hydrophobic chain structure with head groups capable of surrounding carbon nanotube particles to be adsorbed thereonto, such that dispersibility of the carbon nanotube particles produces a more concentrated carbon nanotube solution and a composition including the same.

2. Description of the Related Art

A carbon nanotube may have a nano-sized cylinder structure in which a two-dimensional graphite plate may be rolled. Electron clouds, which may be formed by π-electrons, may cover the surface of the carbon nanotube. The carbon nanotube may be a macromolecule that has various physical properties depending on the diameter, length and/or chirality thereof. The carbon nanotube may have increased mechanical strength, elasticity, chemical stability and/or electric physical properties. The carbon nanotube may be applied to electron emitters, displays, secondary batteries, fuel cells, nano-sized parts and systems and high-performance complexes.

Even though the carbon nanotube may be applied to various fields, if the carbon nanotube is produced using an electric discharge process, then carbon nanotubes that have a diameter of a few nanometers and/or a length corresponding to an aspect ratio of about 1000 may be tangled. Tangled carbon nanotubes may be difficult to disperse in a solution.

A process of adding a dispersant has been used to more uniformly disperse the carbon nanotubes in the solution to avoid the above-mentioned problem. A conventional water-based dispersant may be exemplified by sodium dodecyl benzene sulfonate (NaDDBS), sodium dodecyl sulfate, and TX-100. Sodium dodecyl benzene sulfonate (NaDDBS) is the most well-known dispersant.

The conventional water-based dispersant has lower dispersibility relative to a more concentrated carbon nanotube dispersion solution; as such, it may be difficult to more uniformly disperse the carbon nanotubes at a higher concentration, and precipitation may occur due to agglomeration.

SUMMARY OF THE INVENTION

Example embodiments of the present invention relate to a dispersant for a carbon nanotube solution. Example embodiments of the present invention provide a dispersant having a hydrophobic chain structure with head groups capable of surrounding carbon nanotube particles. The dispersant may be adsorbed onto the carbon nanotube particles such that dispersibility of carbon nanotubes in water is increased, producing a more concentrated carbon nanotube solution.

Other example embodiments of the present invention provide a composition which includes the above dispersant in order to increase the dispersion of carbon nanotubes.

Example embodiments of the present invention provide a dispersant for a more highly concentrated carbon nanotube solution, which may be expressed by any one of the following Formulae 1 to 6.

$$(CF_3(CF_2)_aCH_2CH_2O)_xPO(OR')_y(OCH_2CH_2OH)_z \quad \text{FORMULA 1}$$

In Formula 1, a is an integer ranging from 1 to 30, R' is selected from the group consisting of H, $NH_4$, Li, Na and K, and the following expressions are satisfied: x+y+z=3, x≠0 and y≠0.

$$CF_3(CF_2)_aCH_2CH_2SCH_2CH_2R \quad \text{FORMULA 2}$$

In Formula 2, a is an integer ranging from 1 to 30, and R is selected from the group consisting of a carboxylic acid or salts thereof, a phosphoric acid or salts thereof, and a sulfonic acid or salts thereof.

$$(CF_3(CF_2)_aCH_2CH_2O)PO(OR')(OCH_2CH_2(CF_2)_bCF_3) \quad \text{FORMULA 3}$$

In Formula 3, a and b are independently an integer ranging from 1 to 30, and R' is selected from the group consisting of H, $NH_4$, Li, Na and K.

$$CF_3(CF_2)_aCH_2CH_2R \quad \text{FORMULA 4}$$

In Formula 4, a is an integer ranging from 1 to 30, and R is selected from the group consisting of a carboxylic acid or salts thereof, a phosphoric acid or salts thereof, and a sulfonic acid or salts thereof $$CF_3(CF_2CFR)_aCF_3 \quad \text{FORMULA 5}$$

In Formula 5, a is an integer ranging from 50 to 160, and R is selected from the group consisting of a carboxylic acid or salts thereof, a phosphoric acid or salts thereof, and a sulfonic acid or salts thereof $$CF_3[(CF_2CF_2)_a(CF_2CF(OCF_2CF(CF_3)OCF_2CF_2R)]_xCF_3 \quad \text{FORMULA 6}$$

In Formula 6, a is an integer ranging from 0 to 4, x is an integer ranging from 45 to 160, and R is selected from the group consisting of a carboxylic acid or salts thereof, a phosphoric acid or salts thereof, and a sulfonic acid or salts thereof Other example embodiments of the present invention provide a composition including the above dispersant, an aqueous liquid medium and/or a carbon nanotube.

The aqueous liquid medium may be water or a mixture of water, and one or more polar solvents. The volume ratio of the mixed water and polar solvent(s) may be about 12:8-2:18, or about 8:12, in the aqueous liquid medium. The polar solvent may be selected from the group consisting of methyl alcohol, ethyl alcohol, n-propyl alcohol, isopropyl alcohol, n-butyl alcohol, sec-butyl alcohol, t-butyl alcohol, isobutyl alcohol, ethylene glycol, diethylene glycol, triethylene glycol, propylene glycol, butylene glycol, 1,3-propanediol, 1,4-butanediol, 1,5-pentanediol, 1,2-hexanediol and 1,6-hexanediol. The polar solvent is not limited to the solvents provided.

The carbon nanotube may be selected from the group consisting of a single wall carbon nanotube, a double wall carbon nanotube, a multi wall carbon nanotube and/or a bundle-type carbon nanotube.

In the composition, the weight ratio of the mixed carbon nanotube and dispersant maybe about 1:0.1-1:100.

The composition may include about 0.01-10 wt % carbon nanotube, about 0.001-50 wt % dispersant and about 40-99.989 wt % aqueous liquid medium.

The composition may include an additive. The pH concentration of the dispersed solution may be adjusted to about 2-12 using the additive. The pH concentration may be adjusted to about 4-10. The additive may be a hydroxide. The hydroxide may be selected from the group consisting of sodium hydroxide, potassium hydroxide, calcium hydroxide and ammonium hydroxide. The additive may be an acid. The acid may be selected from the group consisting of a hydrochloric acid, a sulfuric acid, a nitric acid, an acetic acid and a carbonic acid.

According to an example embodiment of the present invention, the dispersant described may have a hydrophobic chain structure with head groups capable of surrounding carbon nanotube particles. The dispersant may adsorbed onto the carbon nanotube particles such that dispersibility of carbon nanotubes in water is increased, producing a more concentrated carbon nanotube solution.

According to other example embodiments, the composition described may exhibit increased dispersion of carbon nanotubes in a higher concentration carbon nanotube solution.

BRIEF DESCRIPTION OF THE DRAWINGS

Example embodiments of the present invention will become readily apparent by reference to the following detailed description when considering in conjunction with the accompanying drawings.

FIG. 1 illustrates the adsorption and dispersion of a dispersant on a surface of a carbon nanotube in a solvent according to example embodiments of the present invention;

FIG. 2 is a histogram showing absorbances of carbon nanotube dispersed solutions using the dispersants and sodium dodecyl benzene sulfonate (NaDDBS) according to example embodiments of the present invention;

FIG. 3 is a graph showing absorbance of the dispersed solution as a function of an isopropyl alcohol content according to example embodiments of the present invention;

FIG. 4 is a histogram showing absorbance of the dispersed solution as a function of a pH of a solvent depending on an additive according to example embodiments of the present invention;

FIG. 5 is a picture of a highly concentrated carbon nanotube dispersed with the dispersant prepared according to example embodiments of the present invention added to water and a highly concentrated carbon nanotube dispersed in NaDDBS added into water; and FIG. 6 is a picture after stirring the dilute solutions, which is made by a highly concentrated carbon nanotube dispersed by the dispersant prepared according to example embodiments of the present invention and a highly concentrated carbon nanotube dispersed in NaDDBS.

DESCRIPTION OF EXAMPLE EMBODIMENTS

Figure 1:
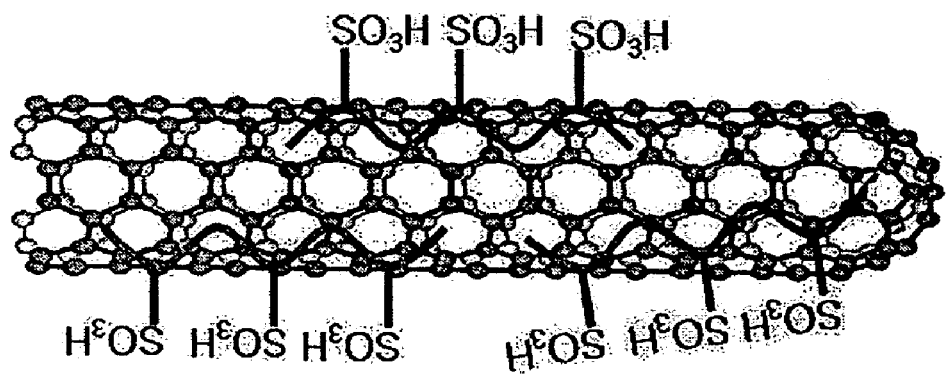
FIGS. 1-6 represent non-limiting example embodiments of the present invention as described herein.

Various example embodiments of the present invention will now be described more fully with reference to the accompanying drawings in which some example embodiments of the invention are shown. In the drawings, the thicknesses of layers and regions may be exaggerated for clarity.

Detailed illustrative embodiments of the present invention are disclosed herein. However, specific structural and functional details disclosed herein are merely representative for purposes of describing example embodiments of the present invention. This invention may, however, may be embodied in many alternate forms and should not be construed as limited to only the embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the invention to the particular forms disclosed, but on the contrary, example embodiments of the invention are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between", "adjacent" versus "directly adjacent", etc.).

The terminology used herein is for the purpose of describing particular embodiments only and is not intended to be limiting of example embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the scope of example embodiments of the present invention.

Spatially relative terms, such as "beneath", "below", "lower", "above", "upper" and the like, may be used herein for ease of description to describe one element or a feature's relationship to another element or feature as illustrated in the Figures. It will be understood that the spatially relative terms are intended to encompass different orientations of the device in use or operation in addition to the orientation depicted in the Figures. For example, if the device in the Figures is turned over, elements described as "below" or "beneath" other elements or features would then be oriented "above" the other elements or features. Thus, for example, the term "below" can encompass both an orientation which is above as well as below. The device may be otherwise oriented (rotated 90 degrees or viewed or referenced at other orientations) and the spatially relative descriptors used herein should be interpreted accordingly.

Also, the use of the words "compound," "compounds," or "compound(s)," refer to either a single compound or to a plurality of compounds. These words are used to denote one or more compounds but may also just indicate a single compound.

It should also be noted that in some alternative implementations, the functions/acts noted may occur out of the order noted in the FIGS. For example, two FIGS. shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments of the present invention belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In order to more specifically describe example embodiments of the present invention, various aspects of the present invention will be described in detail with reference to the attached drawings. However, the present invention is not limited to the example embodiments described.

Example embodiments of the present invention provide a dispersant for a carbon nanotube solution and a composition including the same. Other example embodiments of the present invention provide a dispersant having a hydrophobic chain structure with head groups capable of surrounding the carbon nanotube particles. The dispersant may adsorb onto the carbon nanotube particles such that dispersibility of carbon nanotube particles produces a higher concentrated carbon nanotube solution and a composition including the same.

Hereinafter, a detailed description will be given of a dispersant for a more concentrated carbon nanotube solution and a composition including the same according to example embodiments of the present invention.

Among various surfactants, fluorinated surfactants (wherein fluorine atoms replace hydrogen atoms) may show higher hydrophobicity with respect to their hydrogenated counterparts. Fluorosurfactants may be more effective at reducing surface tension than conventional hydrocarbon-based surfactants. The fluorosurfactants may be based on a perfluoroalkyl moiety, which may constitute all or only part of the total hydrophobic tail group.

As shown in the following Formulae, the dispersant for the more concentrated carbon nanotube solution according to example embodiments of the present invention may include a monomolecule or a polymer with head groups including hydrophobic chains constituted by the perfluoroalkyl moiety. The surfactants (wherein fluorine atoms replace hydrogen atoms) may show higher hydrophobicity, and may be more effective at reducing surface tension than hydrocarbon-based surfactant. Furthermore, a hydrophilic tail portion of the molecule includes a carboxylic acid or salts thereof, a phosphoric acid or salts thereof, or a sulfonic acid or salts thereof The electrostatic repulsion may give more stability during dispersion.

$(CF_3(CF_2)_aCH_2CH_2O)_xPO(OR')_y(OCH_2CH_2OH)_z$ FORMULA 1

In Formula 1, a is an integer ranging from 1 to 30, R' is selected from the group consisting of H, NH4, Li, Na and K, and the following expressions are satisfied x+y+z=3, x≠0 and y≠0.

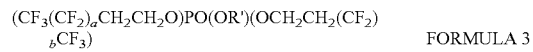
$CF_3(CF_2)_aCH_2CH_2SCH_2CH_2R$ FORMULA 2

In Formula 2, a is an integer ranging from 1 to 30 and R is selected from the group consisting of a carboxylic acid or salts thereof, a phosphoric acid or salts thereof, and a sulfonic acid or salts thereof $(CF_3(CF_2)_aCH_2CH_2O)PO(OR')(OCH_2CH_2(CF_2)_bCF_3)$ FORMULA 3

In Formula 3, a and b are independently an integer ranging from 1 to 30 and R' is selected from the group consisting of H, NH4, Li, Na and K.

$CF_3(CF_2)_aCH_2CH_2R$ FORMULA 4

In Formula 4, a is an integer ranging from 1 to 30, and R is selected from the group consisting of a carboxylic acid or salts thereof, a phosphoric acid or salts thereof, and a sulfonic acid or salts thereof

$CF_3(CF_2CFR)_aCF_3$ FORMULA 5

In Formula 5, a is an integer ranging from 50 to 160 and R is selected from the group consisting of a carboxylic acid or salts thereof, a phosphoric acid or salts thereof, and a sulfonic acid or salts thereof

$CF_3[(CF_2CF_2)_a(CF_2CF(OCF_2CF(CF_3)OCF_2CF_2R)]_xCF_3$ FORMULA 6

In Formula 6, a is an integer ranging from 0 to 4, x is an integer ranging from 45 to 160 and R is selected from the group consisting of a carboxylic acid or salts thereof, a phosphoric acid or salts thereof, and a sulfonic acid or salts thereof.

FIG. 1 illustrates the adsorption and dispersion of the dispersant on a surface of the carbon nanotube in a solvent according to example embodiments of the present invention. After the hydrophobic chains of the dispersant are adsorbed onto the surface of the hydrophobic carbon nanotube, tails that may be located in the solvent surrounding the carbon nanotube to make intervals between the carbon nanotubes regular due to a steric hindrance effect. The steric hindrance effect may decrease re-agglomeration of the carbon nanotubes. Furthermore, due to the hydrophilic tails having electrical charges, repulsive forces may be formed among the carbon nanotubes to retard the re-agglomeration of the particles.

Hereinafter, a description will be given of the composition including the dispersant expressed by any one of Formulae 1 to 6.

According to example embodiments of the present invention, the composition may include the dispersant, an aqueous liquid medium and/or the carbon nanotubes. The aqueous liquid medium may be exemplified by water or a mixture of water and one or more polar solvents. The volume ratio of water and polar solvent mixed in the aqueous liquid medium may be about 12:8-2:18, or about 8:12.

As described above, if the polar solvent is used together as the aqueous liquid medium, then the surface tension may be reduced between the carbon nanotube particles and the medium to increase wetting of the carbon nanotube. The reduced surface tension may increase dispersion of the carbon nanotube in comparison with the use of a single solvent containing only water.

Illustrative, non-limiting examples of the polar solvent useful to the example embodiments of the present invention include methyl alcohol, ethyl alcohol, n-propyl alcohol, isopropyl alcohol, n-butyl alcohol, sec-butyl alcohol, t-butyl alcohol, isobutyl alcohol, ethylene glycol, diethylene glycol, triethylene glycol, propylene glycol, butylene glycol, 1,3-propanediol, 1,4-butanediol, 1,5-pentanediol, 1,2-hexanediol and/or 1,6-hexanediol.

The carbon nanotube may be selected from the group consisting of a single wall carbon nanotube, a double wall carbon nanotube, a multi wall carbon nanotube and a bundle-type carbon nanotube.

In the composition, the weight ratio of the carbon nanotube and the dispersant mix may be about 1:0.1-1:100. The composition may include about 0.01-10 wt % carbon nanotube, about 0.001-50 wt % dispersant and/or about 40-99.989 wt % aqueous liquid medium.

An additive may be added to the dispersed solution, if necessary. The pH concentration of the dispersed solution may be adjusted using the additive to about 2-12, or about 4-10. The additive may be a hydroxide. The hydroxide may be selected from the group consisting of sodium hydroxide, potassium hydroxide, calcium hydroxide and ammonium hydroxide. The additive may be an acid. The acid may also be selected from the group consisting of a hydrochloric acid, a sulfuric acid, a nitric acid, an acetic acid and a carbonic acid. The acidic or basic additive may increase the solubility of the dispersant to the aqueous liquid medium and/or may provide electrostatic repulsive forces to the carbon nanotube particles to retard the particles from agglomerating. The dispersion state of the carbon nanotubes may be more stable, improving dispersibility. If the pH concentration is more than about 12 or is less than about 2, the concentration of ions may be increased to reduce the thickness of a double layer. Increased thickness of a double layer may lead to a decrease in the repulsive forces, reducing dispersibility.

A further understanding of the example embodiments of the present invention may be obtained through the following examples which are set forth to illustrate, but are not to be construed as to limit the example embodiments of the present invention.

EXAMPLE 1

20 mg (an amount ten times as much as an amount of a carbon nanotube to be added) of $(CF_3(CF_2)_{15}CH_2CH_2O)PO(ONH_4)_2$ the dispersant expressed by Formula 1 was dissolved in 20 ml of water. 2 mg of multi-wall carbon nanotubes were added to the resulting solution and then dispersed therein for about 10 hours using a sonic bath. Subsequently, centrifugation was conducted at 5600 rpm for about 5 min to produce a carbon nanotube solution.

A portion of the dispersion was sampled to measure the absorbance at 700 nm using UV-Vis-spectroscopy (JASCO (V-560), Absorbance mode, scanning speed of 400 nm/min). A dispersant solution having no carbon nanotubes was used as a standard solution. The measurements were consistent with a concentration of the solution having the carbon nanotubes desirably dispersed therein.

EXAMPLE 2

The procedure of Example 1 was repeated to produce a carbon nanotube solution with the exception that $CF_3(CF_2)_{15}CH_2CH_2SCH_2CH_2COOLi$, expressed by Formula 2, was used as the dispersant during the production of the carbon nanotube solution.

EXAMPLE 3

The procedure of Example 1 was repeated to produce a carbon nanotube solution with the exception that $(CF_3(CF_2)_{14}CH_2CH_2O)PO(OH)_2$, expressed by Formula 3, was used as the dispersant during the production of the carbon nanotube solution.

EXAMPLE 4

The procedure of Example 1 was repeated to produce a carbon nanotube solution with the exception of $CF_3(CF_2)_{15}CH_2CH_2SO_3H$, expressed by Formula 4, was used as a dispersant during the production of the carbon nanotube solution.

EXAMPLE 5

The procedure of Example 1 was repeated to produce a carbon nanotube solution with the exception that $(CF_3(CF_2)_{15}CH_2CH_2O)PO(ONH_4)(OCH_2CH_2OH)$, expressed by Formula 1, was used as the dispersant during the production of the carbon nanotube solution.

EXAMPLE 6

The procedure of Example 1 was repeated to produce a carbon nanotube solution with the exception that $CF_3[(CF_2CF_2)_3(CF_2CF(OCF_2CF(CF_3)OCF_2CF_2R)]_{105}CF_3$, expressed by Formula 6, was used as the dispersant during the production of the carbon nanotube solution.

EXAMPLE 7

20 mg (an amount ten times an amount of a carbon nanotube to be added) of $CF_3[(CF_2CF_2)_3(CF_2CF(OCF_2CF(CF_3)OCF_2CF_2R)]_{105}CF_3$ a dispersant expressed by Formula 6 was added to 20 ml of water and dissolved. 2 mg of double wall carbon nanotubes were added to the resulting solution and then dispersed therein for about 10 hours using a sonic bath. Centrifugation was conducted at 5600 rpm for about 5 min to produce a carbon nanotube solution.

Absorbance of the carbon nanotube solution was measured at 700 nm using UV-Vis-spectroscopy (JASCO(V-560), Absorbance mode, scanning speed of 400 nm/min). A dispersant solution having no carbon nanotube was used as a standard solution.

EXAMPLES 8-11

The procedure of Example 7 was repeated to produce a carbon nanotube solution with the exception that a mixture of 16 ml of water and 4 ml of isopropyl alcohol, a mixture of 8 ml of water and 12 ml of isopropyl alcohol, a mixture of 4 ml of water and 16 ml of isopropyl alcohol, and a mixture of 2 ml of water and 18 ml of isopropyl alcohol, respectively, were used as solvents during the production of the carbon nanotube solution.

EXAMPLE 12

The procedure of Example 7 was repeated to produce a carbon nanotube solution with the exception that 20 ml of isopropyl alcohol was used as the solvent during the production of the carbon nanotube solution.

EXAMPLE 13

20 mg (an amount ten times as much as that of a carbon nanotube to be added) of $(CF_3(CF_2)_{15}CH_2CH_2O)PO(OH)_2$ a dispersant, expressed by Formula 3, were added to 20 ml of water and dissolved. 2 mg of single wall carbon nanotubes were added to the resulting solution and then dispersed therein for about 10 hours using a sonic bath. After the dispersion, centrifugation was conducted at 5600 rpm for about 5 min to produce a carbon nanotube solution.

Absorbance of the carbon nanotube solution was measured at 700 nm using UV-Vis-spectroscopy (JASCO(V-560), Absorbance mode, scanning speed of 400 nm/min). A dispersant solution having no carbon nanotube was used as a standard solution.

EXAMPLES 14-22

The procedure of Example 13 was repeated to produce a carbon nanotube solution with the exception that a sodium hydroxide (NaOH) aqueous solution was used as the solvent during the production of the carbon nanotube solution to adjust the pH to 3.3, 3.9, 6.4, 7.4, 8.6, 9.6, 11.0, 12.8, and 13.1, respectively.

COMPARATIVE EXAMPLE 1

The procedure of Example 1 was repeated to produce a carbon nanotube solution with the exception that sodium dodecyl benzene sulfonate (NaDDBS) was used as the dispersant during the production of the carbon nanotube solution.

Figure 2:
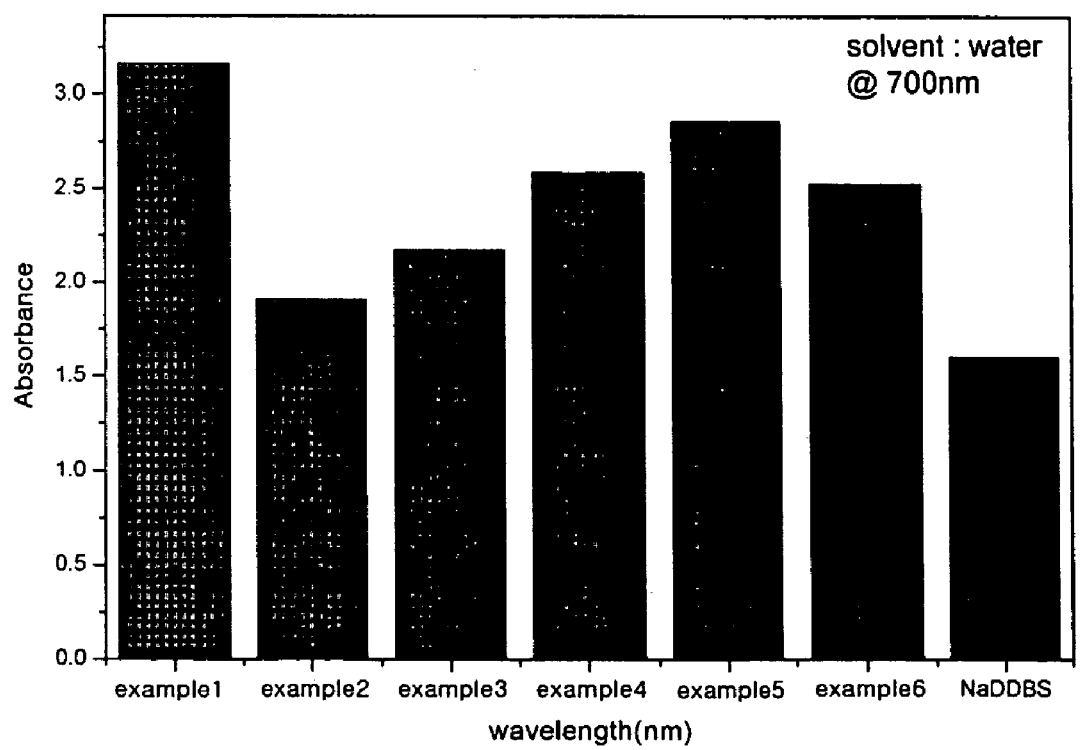

Absorbances of carbon nanotube solutions that were produced according to Examples 1-6 and Comparative Example 1 were measured depending on the type of dispersant, and the results are shown in FIG. 2.

As shown FIG. 2, the dispersant prepared according to example embodiments of the present invention expressed by any one of Formulae 1-6 has a higher absorbance than a conventional water-based dispersant (e.g., sodium dodecyl benzene sulfonate (NaDDBS)). The dispersant described may more uniformly disperse the carbon nanotubes.

Absorbances of the carbon nanotube solutions that were produced according to Examples 7-12 were measured depending on the content of isopropyl alcohol. The results are shown in FIG. 3.

Figure 3:
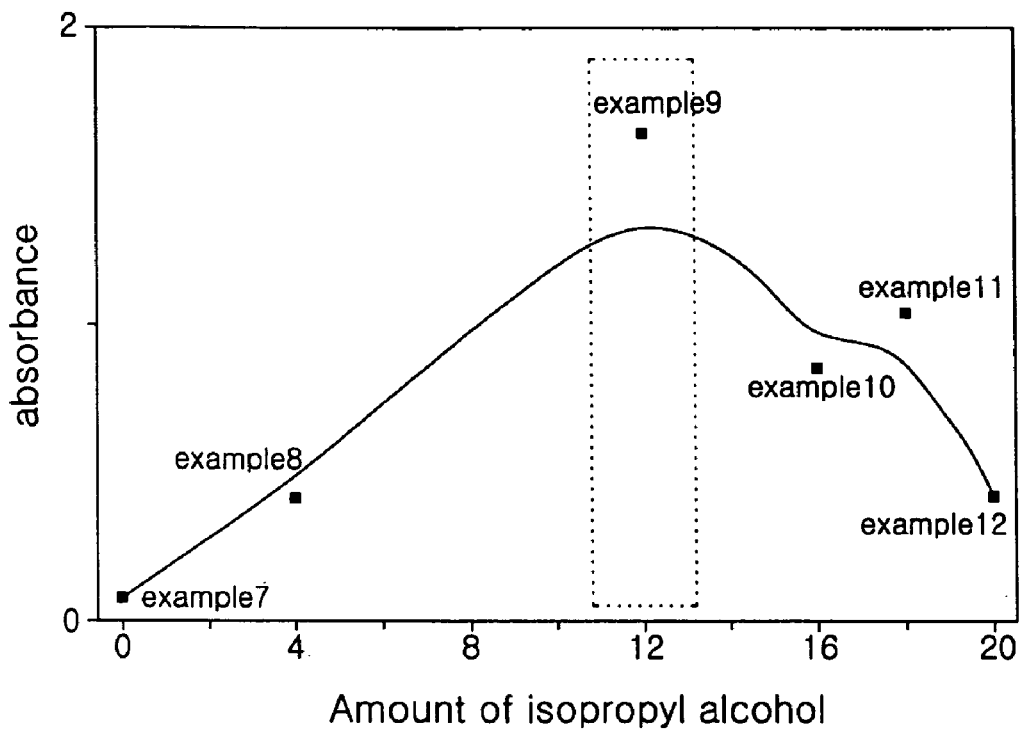

As shown in FIG. 3, the absorbance of the carbon nanotube solution is highest when the content of isopropyl alcohol is about 60 vol %.

Absorbances of the carbon nanotube solutions that were produced according to Examples 13-22 were measured depending on the pH concentration of the solvent, which is controlled by the addition of NaOH. The results are shown in FIG. 4.

Figure 4:
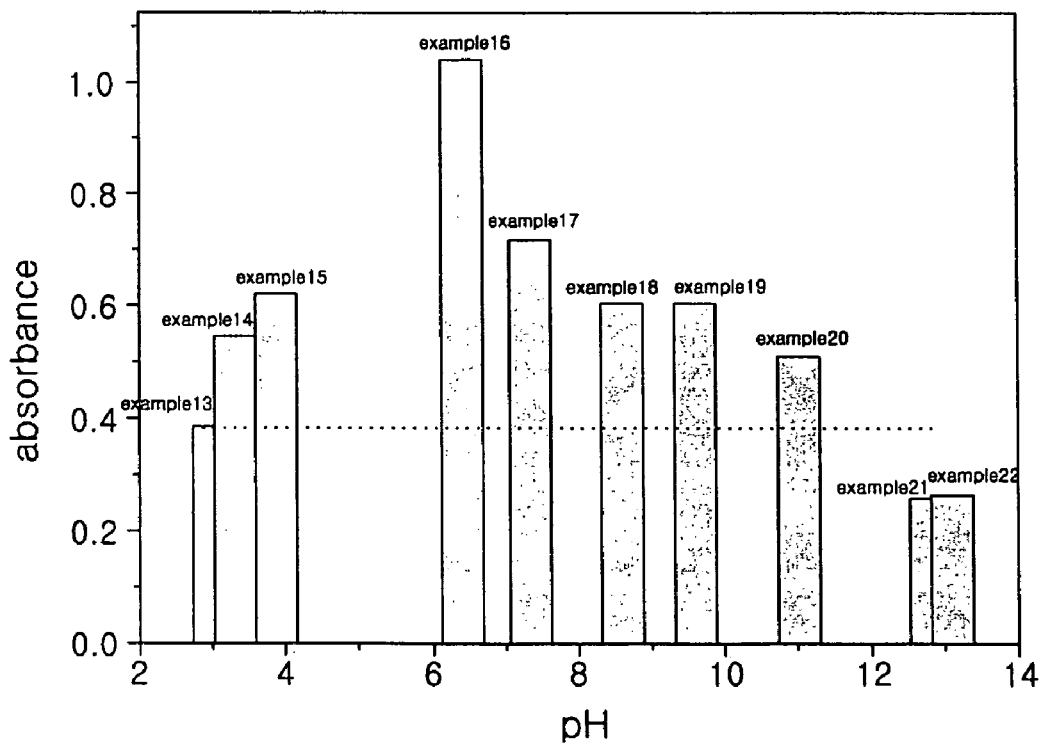

As shown in FIG. 4, the absorbance is highest when the pH concentration of the solvent is set to about 6-8 by adding NaOH.

According to the example embodiments of the present invention, if the dispersant is added to about 20 ml of solvent such that the ratio of the dispersant to the carbon nanotube is about 10, then it may be possible to disperse the carbon nanotubes in a concentration of about 600 mg/20 ml.

In order to evaluate dispersion of the more concentrated carbon nanotube solution, 20 ml of solvent, 600 mg of carbon nanotubes, $CF_3[(CF_2CF)_3(CF_2CF(OCF_2CF(CF_3)OCF_2CF_2SO_3H)]_{105}CF_3$ (the dispersant expressed by Formula 6) or NaDDBS were mixed with each other such that the weight ratio of $CF_3[(CF_2CF)_3(CF_2CF(OCF_2CF(CF_3)OCF_2CF_2SO_3H)]_{105}CF_3$ to the carbon nanotube was about 1.5, producing the more highly concentrated carbon nanotube solution. Dispersion of the more concentrated carbon nanotube solution was observed. The results are shown in FIGS. 5 and 6.

Figure 5:
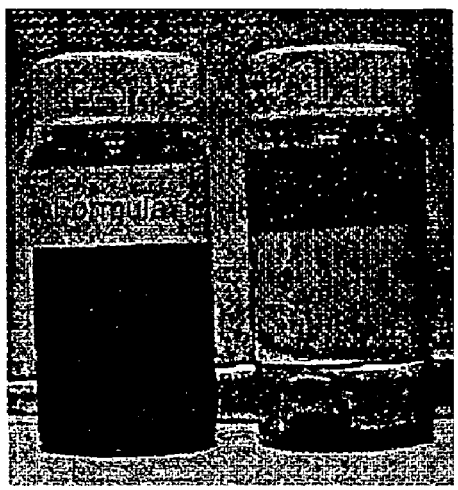

As shown in FIG. 5, when 0.1 g of the more concentrated dispersed solution is dropped on 19.9 g of water, agglomerates are precipitated in the solution dispersed using NaDDBS. Uniform dispersion is achieved if the dispersant of Formula 6 is used. Thus, the NaDDBS may not disperse the carbon nanotubes in a higher concentration, but precipitates the carbon nanotubes due to agglomeration.

Figure 6:
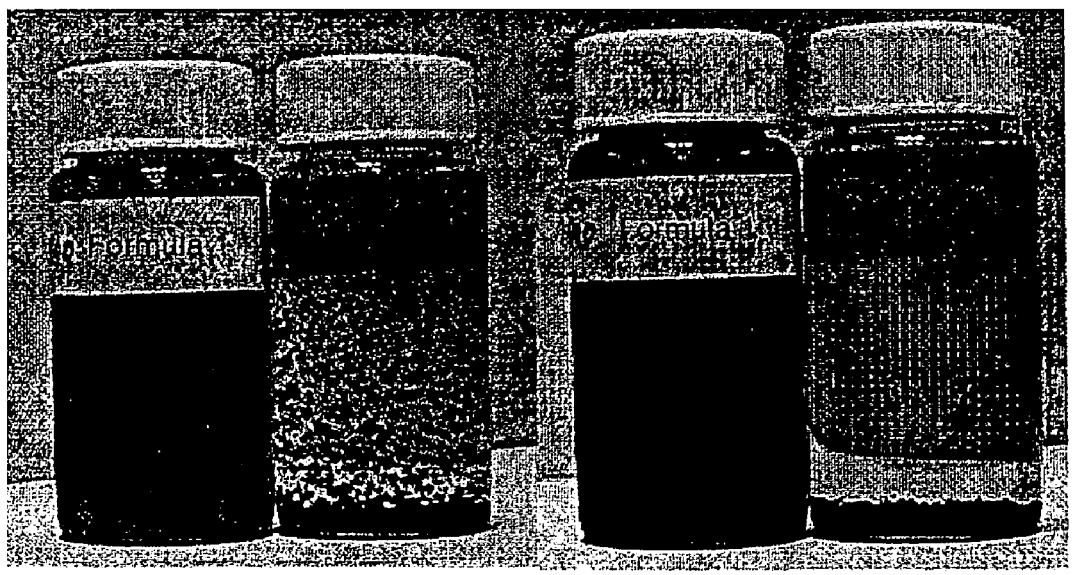

FIG. 6 shows the results after stirring for about 1 hr the diluted solution which is shown in FIG. 5. In the dispersed solution using NaDDBS, agglomerates are not dispersed, but are precipitated after about 15 min. When using the dispersant of Formula 6, precipitation may not occur.

The dispersant, which is expressed by any one of Formulae 1 to 6, may be used in a more concentrated carbon nanotube solution. The dispersant may have a hydrophobic chain structure capable of being surrounded by carbon nanotube particles, adsorbing thereonto. The dispersed solution prepared according to example embodiments of the present invention may include the dispersant and an organic solvent. The dispersed solution may further include an additive, such as NaOH. It may be possible to produce the more concentrated carbon nanotube solution exhibiting an increase in dispersion of the carbon nanotubes and/or more stability.

The foregoing is illustrative of the example embodiments of the present invention and is not to be construed as limiting thereof. Although a few example embodiments of the present invention have been described, those skilled in the art will readily appreciate that many modifications are possible in the example embodiments without materially departing from the novel teachings and advantages of the present invention. Accordingly, all such modifications are intended to be included within the scope of this invention as defined in the claims. In the claims, means-plus-function clauses are intended to cover the structures described herein as performing the recited function, and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The present invention is defined by the following claims, with equivalents of the claims to be included therein.

What is claimed is:
1. A composition comprising:
   a dispersant, which is expressed by one of the following Formulae 1 and 3-6:

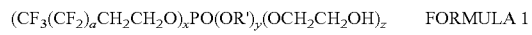

$$(CF_3(CF_2)_a CH_2CH_2O)_x PO(OR')_y (OCH_2CH_2OH)_z \quad \text{FORMULA 1}$$

wherein a is an integer ranging from 1 to 30, R' is selected from a group consisting of H, $NH_4$, Li, Na and K, and further wherein the following expressions are satisfied: $x+y+z=3$, $x \neq 0$, and $y \neq 0$,

$$(CF_3(CF_2)_a CH_2CH_2O)PO(OR')(OCH_2CH_2(CF_2)_b CF_3) \quad \text{FORMULA 3}$$

wherein a and b are independently an integer ranging from 1 to 30, and R' is selected from a group consisting of H, $NH_4$, Li, Na and K, and further wherein $a \neq b$,

$$CF_3(CF_2)_a CH_2CH_2R \quad \text{FORMULA 4}$$

wherein a is an integer ranging from 1 to 30 and R is selected from a group consisting of a phosphoric acid or salts thereof, and a sulfonic acid or salts thereof, $$CF_3(CF_2CFR)_aCF_3 \qquad \text{FORMULA 5}$$

wherein a is an integer ranging from 50 to 160 and R is selected from a group consisting of a carboxylic acid or salts thereof, a phosphoric acid or salts thereof, and a sulfonic acid or salts thereof; and $$CF_3[(CF_2CF_2)_a(CF_2CF(OCF_2CF(CF_3)OCF_2CF_2R)]_x CF_3 \qquad \text{FORMULA 6}$$

wherein a is an integer ranging from 0 to 4, x is an integer ranging from 45 to 160 and R is selected from a group consisting of a carboxylic acid or salts thereof, and a phosphoric acid or salts thereof;
an aqueous liquid medium; and
a carbon nanotube,
wherein a weight ratio of the carbon nanotube and the dispersant when mixed is about 1:0.1-1:100.

2. The composition as set forth in claim 1, wherein the aqueous liquid medium is water or a mixture of water and one or more polar solvents.

3. The composition as set forth in claim 2, wherein each of the polar solvents is selected from a group consisting of methyl alcohol, ethyl alcohol, n-propyl alcohol, isopropyl alcohol, n-butyl alcohol, sec-butyl alcohol, t-butyl alcohol, isobutyl alcohol, ethylene glycol, diethylene glycol, triethylene glycol, propylene glycol, butylene glycol, 1,3-propanediol, 1,4-butanediol, 1,5-pentanediol, 1,2-hexanediol and 1,6-hexanediol.

4. The composition as set forth in claim 2, wherein a volume ratio of water and the polar solvents when mixed is about 2:18-12:8 in the aqueous liquid medium.

5. The composition as set forth in claim 4, wherein the volume ratio is about 8:12.

6. The composition as set forth in claim 1, further comprising an additive.

7. The composition as set forth in claim 6, wherein a pH concentration of the composition is about 2 to 12.

8. The composition as set forth in claim 6, wherein the additive is a hydroxide.

9. The composition as set forth in claim 8, wherein the hydroxide is selected from a group consisting of sodium hydroxide, potassium hydroxide, calcium hydroxide and ammonium hydroxide.

10. The composition as set forth in claim 6, wherein the additive is an acid.

11. The composition as set forth in claim 10, wherein the acid is selected from a group consisting of a hydrochloric acid, a sulfuric acid, a nitric acid, an acetic acid and a carbonic acid.

12. The composition as set forth in claim 1, wherein the carbon nanotube is selected from a group consisting of a single wall carbon nanotube, a double wall carbon nanotube, a multi wall carbon nanotube and a bundle-type carbon nanotube.

13. The composition as set forth in claim 1, wherein a percent-by-weight of the carbon nanotubes, dispersant and aqueous liquid medium is about 0.01-10 wt % carbon nanotubes; about 0.001-50 wt % dispersant; and about 40-99.989 wt % aqueous liquid medium.

* * * * *